(12) United States Patent
Rasch-Menges et al.

(10) Patent No.: US 9,554,703 B2
(45) Date of Patent: Jan. 31, 2017

(54) DIABETES CARE SYSTEM FOR DETECTION OF AN ANALYTE AND METHOD FOR SELECTIVE DATA TRANSMISSION

(75) Inventors: Jürgen Rasch-Menges, Schwetzingen (DE); Paul Jansen, Mannheim (DE); Hans-Peter Haar, Wiesloch (DE); Ulrich Haueter, Grosshöchstetten (CH); Andreas Poredda, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1513 days.

(21) Appl. No.: 11/763,004

(22) Filed: Jun. 14, 2007

(65) Prior Publication Data

US 2007/0299324 A1 Dec. 27, 2007

(30) Foreign Application Priority Data

Jun. 21, 2006 (EP) .................................... 06012693

(51) Int. Cl.
*A61B 5/00* (2006.01)
*A61B 5/145* (2006.01)
*G01N 33/487* (2006.01)
*H04L 29/08* (2006.01)
*A61N 1/372* (2006.01)

(52) U.S. Cl.
CPC ......... *A61B 5/0002* (2013.01); *A61B 5/14532* (2013.01); *G01N 33/48792* (2013.01); *H04L 67/14* (2013.01); *A61N 1/37252* (2013.01); *A61N 1/37276* (2013.01)

(58) Field of Classification Search
CPC ..... A61B 5/002; A61B 5/14532; H04L 67/14; G01N 33/48792; A61N 1/37252; A61N 1/37276
USPC .................................................. 600/365, 366
See application file for complete search history.

(56) References Cited

U.S. PATENT DOCUMENTS

| | | | |
|---|---|---|---|
| 5,564,429 A | | 10/1996 | Bornn et al. |
| 5,839,100 A | * | 11/1998 | Wegener ........................ 704/220 |
| 5,907,556 A | * | 5/1999 | Hisanaga et al. ............. 370/468 |
| 2001/0019309 A1 | | 9/2001 | Saeki et al. |
| 2001/0027384 A1 | | 10/2001 | Schulze et al. |
| 2002/0103447 A1 | * | 8/2002 | Terry ............................ 600/595 |
| 2004/0054263 A1 | | 3/2004 | Moerman et al. |

(Continued)

FOREIGN PATENT DOCUMENTS

| | | |
|---|---|---|
| EP | 1437647 A2 | 7/2004 |
| EP | 1870026 A1 | 12/2007 |

(Continued)

*Primary Examiner* — Michael Kahelin
*Assistant Examiner* — Tho Tran
(74) *Attorney, Agent, or Firm* — Harness Dickey (57) ABSTRACT

A diabetes care system for detection of an analyte and method for selective data transmission are disclosed. The diabetes care system has a mobile component and a base station, wherein a data transmission occurring between the mobile component and the base station within a time interval in which a wireless communication link exists, wherein is selectively performed in such a manner that within the time interval, a first partial set of the data is transmitted from the mobile component to the base station. The first partial set is selected using a processor-controlled selection algorithm in such a manner that the data transmitted in the time interval is representative of the entirety of the data stored in the mobile component.

8 Claims, 4 Drawing Sheets

(56) References Cited

U.S. PATENT DOCUMENTS

| | | |
|---|---|---|
| 2004/0122488 A1 | 6/2004 | Mazar et al. |
| 2004/0122489 A1* | 6/2004 | Mazar ................ A61N 1/37282 607/60 |
| 2004/0215270 A1 | 10/2004 | Ritscher et al. |
| 2004/0260189 A1* | 12/2004 | Eggers et al. ................ 600/509 |
| 2005/0038680 A1* | 2/2005 | McMahon ........................ 705/3 |
| 2005/0096511 A1* | 5/2005 | Fox et al. ..................... 600/300 |
| 2006/0122469 A1 | 6/2006 | Martel |
| 2007/0239116 A1* | 10/2007 | Follman et al. .............. 604/189 |
| 2008/0114417 A1* | 5/2008 | Leyde ............................. 607/60 |

FOREIGN PATENT DOCUMENTS

| | | |
|---|---|---|
| JP | 2001241965 A | 9/2001 |
| WO | 03/066159 A2 | 8/2003 |

* cited by examiner

DIABETES CARE SYSTEM FOR DETECTION OF AN ANALYTE AND METHOD FOR SELECTIVE DATA TRANSMISSION

FIELD OF THE INVENTION

The present invention relates generally to diabetes care, and in particular to a diabetes care system for detection of an analyte and method for selective data transmission.

BACKGROUND OF THE INVENTION

Diabetes care systems are used for detecting analytes relevant for the treatment of diabetes mellitus in the human body and/or for treatment, in particular by injection of medicaments. Important examples are blood glucose meters or insulin pumps. Modern diabetes care systems support their users by logging performed actions and thus providing them for later analysis. In this manner, so-called "history files" are created in the course of a longer usage duration.

Like the log data of executed actions, analysis data may also be stored in diabetes care systems. Especially in analysis systems which are wearable on the body (invasive or noninvasive) and implantable in the body, a frequent, even practically continuous measurement and determination of the analytes occurs, in which a large quantity of measurement and/or analysis data are obtained. The temporarily stored data must be transmitted from time to time to a base station, such as a PC.

For this purpose, wired interfaces or wireless interfaces having corresponding interface protocols are frequently used in devices wearable on the body. In implanted devices, the data transmission is always performed wirelessly, of course. In "classical" data transmission, all of the data material present is typically downloaded. A sequential transmission occurs, the data being transmitted in the sequence of their generation (first-in-first-out) or in the reverse sequence of generation (last-in-first-out).

In this classical procedure, it is assumed that the data link exists at least for the duration of the transmission of all data. It may typically not be interrupted. The user is conscious that the data transmission occurs, because he has actively initiated the transmission and monitors the procedure. The software used for data transmission typically also indicates the course of the transmission, for example, as a graphic and/or as a percentage number.

This transmission of the data is perceived by the users as quite uncomfortable. They see themselves as "bound" to the base station, because the transmission may not be interrupted and they may not move away from the base station during the data transmission.

To increase the operator comfort, systems are required in which the communication between the mobile component, which is wearable on or in the body, and the base station is designed as "on-demand", without having to be initiated or monitored by the user. A wireless communication occurs automatically when the user brings the mobile component in proximity to the base station. The devices recognize the proximity of the particular partner component automatically. Establishing the link is therefore very comfortable and user-friendly for the user.

A data transmission can only be performed when the user stays close enough to the base station. The link duration which is available for a communication of this type between a mobile component worn on the body and the base station changes as a function of the dwell time of the user in proximity to the base station. The time duration usable for data transmission is thus unknown to the system. Using the diabetes care systems known in the prior art, reliable data transmission is not possible in the event of varying and unknown link duration.

In addition, special problems exist with the use of diabetes care systems:

On one hand, these systems assume widely important vital medical functions with high complexity. Intervention in the regulation system of the human body, as can be performed on the basis of the data obtained by such systems or by the systems directly, is otherwise typically performed by highly qualified medical personnel and under their continuous observation, for example, in an intensive care unit. However, the operator of the diabetes care system, such as an insulin pump, is the patient, who is typically a medical layperson and who can not completely oversee the effects of an intervention in the system.

On the other hand, diabetics only have restricted power of movement and reduced attentiveness because of their illness, especially in the advanced stage. This can result in malfunctions and incorrect settings of the device or can result in deviating settings, such as an incorrectly regulated insulin dose, not being noted. This can cause severe health damage in the patients. It is also important for this reason to log the actions of the patient and transmit them regularly to a base station, which can assume analysis and alarm functions.

Because of the problems described above, there is a significant risk that with a wireless communication link between the device carried by the person and the base station, the entire link duration for complete transmission of all data cannot be reliably ensured.

SUMMARY OF THE INVENTION

It is therefore against the above background that the present invention provides a diabetes care system in which a data transmission is achieved from a mobile component carried by a person to a base station, in consideration of the problems and requirements explained above.

Embodiments of the diabetes care system according to the present invention are explained in greater detail on the basis of the following drawings. The special features shown can be used individually or in combination to provide various embodiments of the present invention. For example, an analysis system is described here as a possible embodiment of the diabetes care system without restricting the generality.

DETAILED DESCRIPTION

In one embodiment, the diabetes care system according to the present invention for use on the human body comprises a mobile component and a base station. The mobile component is wearable on the body or can be implemented in the body and includes a memory for storing data and a communication unit for transmitting data to the base station. The base station has a communication unit for wireless reception of data from the mobile component and a memory unit for storing transmitted data. Optionally, the base station also has an output unit for displaying data which have been transmitted by the mobile component. The data transmission between the mobile component and the base station occurs within a time interval in which a wireless communication link exists. Because the time interval for data transmission is unknown in principle, a selective data transmission is performed, wherein a first partial set of data being transmitted within the first time interval. The first partial set of data is selected using a processor-controlled selection algorithm in such a manner that the data transmitted in the time interval is representative of the entirety of the data stored in the mobile component.

In the scope of the present invention it has been established that a short transmission time is to be expected precisely in diabetes care systems, because the diabetic frequently does not perceive and/or monitor the wireless communication between the mobile component worn on the body and the base station because of restricted attentiveness. Therefore, the data set which can be transmitted during the existing connection is frequently only a fraction of the data stored in the mobile component.

By suitable selection of the data, a reliable statement about the entirety of the data can already be made using a relatively small amount of selected and transmitted data. For this purpose, the data are in one embodiment prioritized in such a manner that the data whose information content is highest are preferentially transmitted. Because the selected data in the first partial set represent the entirety of the data, it is not necessary to transmit and/or analyze all data to obtain a sufficiently precise information overview of the entirety of the data.

In one embodiment, the mobile component has a continuously operating and measuring measurement unit which is implanted in the body. Typically, measured values from a longer period of time, up to multiple days, are contained in the memory of the mobile component. Using the present invention, the most precise possible representation of the entirety of the measured values is already generated by a small partial set from this large number of measured values.

Because the measured values and/or their analysis is used for analyzing and evaluating control variables, namely in blood sugar measurement devices for establishing the insulin dose to be administered, for example, the most current measured values are typically especially important. Therefore, at least a part of the first partial set of the selected data or measured values in one embodiment is transmitted in a sequence to the base station which is reversed from the sequence of its generation ("last-in-first-out principle"). The measured value measured most recently is transmitted first. This principle does not have to be applied strictly, because it can be combined with other criteria of transmission which are in the foreground. In principle, it is also true here that the information content of the measured value is decisive, not solely the time of its creation.

To obtain the best possible image of the entirety of the data, in general two strategies are possible:
1. The selection of the data from the entirety can be performed using a fixed raster of data which relates to equidistant times.
2. The data of the first partial set are selected in such a manner that a fixed raster is avoided, i.e., the time interval between two selected items of data is not equidistant.

In one embodiment, in which the first partial set of the data is selected in a fixed time raster, the time interval between two selected items of data being equidistant, a uniform overview of the data is generated from the entirety. The selection of the data can then be successively refined, after the first partial set of the data has been transmitted from the mobile component to the base station, by shifting the raster, for example, in such a manner that the first value to be selected lies between two items of data of the first partial set. Alternatively, the equidistant time interval between the selected items of data can also be reduced.

The selection using a constant raster offers a good and rapid overview of the entirety of the data. This method is to be applied in particular if none of the selected measured values appears to be an outlier. However, periodic errors are not reliably recognized with a constant raster. Outliers, i.e., data which lies above a medically acceptable limit, or measurement errors, are not necessarily detected with a fixed raster.

The data of the first partial set are selected using a selection algorithm in which a probability function is implemented. The time interval between each two chronologically neighboring selected items of data of the first partial set differs. The selected items of data of the first partial set are selected according to a probability density.

Higher order "meta-information" can also be implemented in the function. This "meta-information" can be generated by the diabetes care system or the analysis system and/or the mobile component itself if it is a "self-teaching" system. For this purpose, information is obtained from the past and the analysis of the data already selected and transmitted during earlier data transmission, for example, about when outlier measured values occur more frequently. If in the past outliers have occurred more frequently in the morning, the probability that outlier values will also be detected in the morning in the current values present in the memory of the mobile component is increased. The selection algorithm may be changed in such a manner that values are increasingly queried in the morning in particular.

Instead of the probability function, the selection algorithm can also be based on a random function, so that the selected data of the first partial set is selected "randomly". The time interval of each two neighboring selected items of data is then typically also different and not equidistant, so that the problems upon the occurrence of periodic errors are avoided.

The expected duration of the first time interval for the data transmission in one embodiment is also determined from the data transmissions already performed between the mobile component and the base station. The expected data set which can be transmitted in the time interval of the existing communication link may also be determined from the data transmissions which have already occurred. This time duration and/or the amount of the data is a measure of the probability that the same link duration is available in the data transmission occurring now or the next data transmission between the mobile component in the base station and/or the same number of items of data can be transmitted. It is assumed that the patient displays an approximately uniform behavior pattern. In particular if the multiple data transmissions which have already occurred can be analyzed, the prediction of the next transmission duration can be made more precise. The available time interval of data transmission can thus be used effectively.

The first partial set of the data which has been transmitted from the mobile component to the base station during a data transmission in one embodiment is registered in the diabetes care system. In one embodiment, it is useful if the already transmitted data is noted both in the mobile component and also in the base station. Alternatively, a marker is set in only one of the two devices. If a data transmission is aborted early, for example, because the user moves away from the base station with his mobile component, and this also does not correspond to his predicted behavior pattern, the terminated transmission can be continued during the next data transmission. In this case, already transmitted data does not have to be transmitted by the mobile component to the base station once again. The efficiency of the data transmission from the mobile component to the base station thus increases. In a preferred embodiment of the diabetes care system according to the present invention, the already transmitted data of the first partial set are erased from the memory of the mobile component.

Mobile components which are "wearable on the body" are also understood to include those which can be brought into contact with the body. An example is an injection pen for injecting a medicament, such as insulin, for which dosing information is to be transmitted to the base station. A mobile device of this type is only briefly worn on the body, namely during the application of the medication.

The term "data" is understood in its general form in the scope of the present invention and comprises all information which is transmitted between a mobile component and a base station of a diabetes care system. This includes, for example, measured values of blood parameters, such as blood sugar, dosing volumes, in particular of injection pens, delivery volumes of pumps, in particular insulin pumps, or measured pressure curves. Time values are also included by the term "data", which can be generated by an internal clock or a counter and can be provided as absolute or relative time. In this way, the time of the occurrence of the measured values can be detected and transmitted. Data can additionally be measured electrical resistances, voltages, or currents. Optically detected values (photometry) or other state information are also subsumed under the term "data" in the scope of the present invention.

Figure 1:
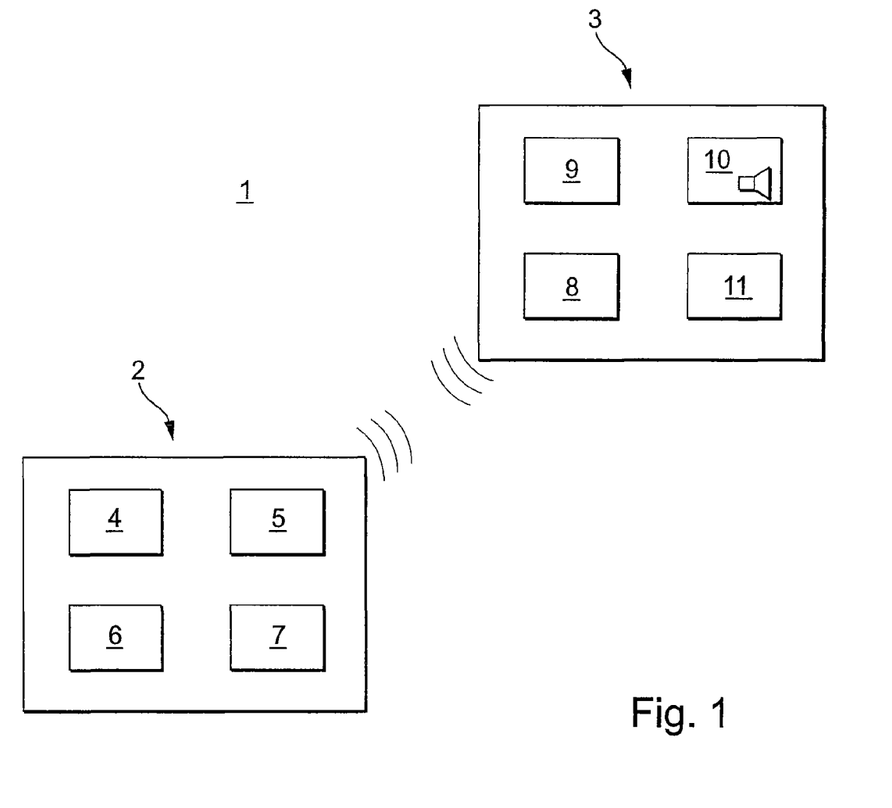
FIG. 1 shows an analysis system having an analysis device and a base station.

The analysis system 1 illustrated in FIG. 1 comprises an analysis device 2, which is wearable or implantable on the body as a mobile component, and a separate base station 3.

The analysis device 2 contains a measuring unit 4 for detecting an analyte and generating measured values suitable for analysis. Furthermore, it includes a communication unit 5, a processor 6, and a memory 7 for storing measured values. The measured values form data which can be transmitted to the base station in the event of an existing communication link. A first partial set of the measured values is selected using a selection algorithm, which in one embodiment is controlled by the processor 6 of the analysis device 2.

In one embodiment, the first partial set of the measured values is already selected before beginning the data transmission between the analysis device 2 and the base station 3. Therefore, all measured values to be transmitted are available when a data link is established between the analysis device 2 and the base station 3, so that they can be transmitted immediately.

The base station 3 comprises a communication unit 8 for wirelessly receiving measured values of the analysis device 2, a memory unit 9 for storing the measured values transmitted by the analysis device 2, and an output unit 10 for displaying the measured values. The output unit 10 can also comprise a loudspeaker in addition to a display, to output acoustic signals and/or the measured value in the form of speech.

The base station 3 in one embodiment includes an alarm unit 11, to output an optical and/or acoustic warning message if the number of transmitted measured values falls below a lower limit. The alarm unit 11 can comprise a display, an optical light indicator, and/or a loudspeaker. The warning message can be generated in particular if too few measured values have been transmitted from the analysis device 2 to the base station 3 to make a reliable statement about the entirety of the measured values stored in the analysis unit.

To establish a communication link between the communication unit 5 of the analysis device 2 and the communication unit 8 of the base station 3, the base station 3 transmits a query on a defined frequency and at a defined transmission power. The base station 3 is referred to as the "master", while the analysis device 2 is the "slave", so that there is a "master-slave relationship" between the two devices. As the slave, the analysis device 2 listens on the same frequency for an incoming query from the base station 3. The transmission power can be designed in such a manner that the analysis device recognizes that the distance has fallen below a defined distance on the basis of the increase of the signal strength. It is also possible to measure the bidirectional data transmission time between the communication unit 5 and the communication unit 8.

If the distance between the analysis device 2 and the base station 3 falls below the predefined distance, the analysis device 2 answers the query of the base station 3. The link is established between the communication units 5, 8. Optionally, a waiting time can be established before beginning the actual data transmission, e.g., to recognize a connection which is too brief or possibly undesired or to adjust the data transmission parameters between the two devices, i.e., to set the speed of the data transmission, the transmission power, etc.

If all conditions are fulfilled, the analysis device 2 (in one embodiment, also without a direct query from the base station 3) transmits the first partial set of the measured values to the master, i.e., the base station 3. Dispensing with the query of the base station 3 shortens the time needed for the data exchange.

The analysis device 2 in one embodiment is moved from its "rest state" into an "active state" by a pulse, a signal, or a command of the base station 3. The rest state is an energy-saving mode or a mode having reduced transmission power. The radiation load of the patient who carries the analysis device 2 is thus reduced; in addition, energy is saved.

Figure 2:
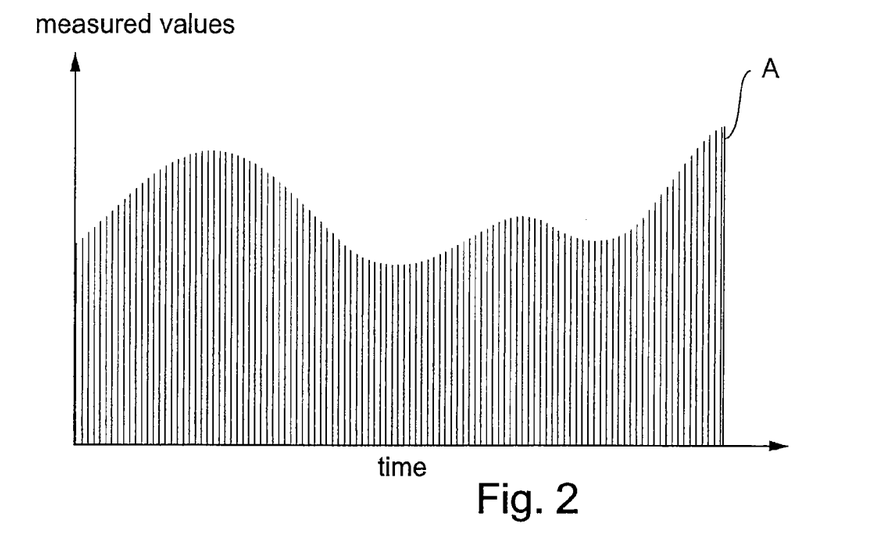
FIG. 2 shows a graph of the time curve of the measured values stored in a memory of the analysis device.

FIG. 2 shows measured values stored in the analysis device 2. The entirety of all discrete measured values is shown, which have been measured at equidistant time intervals.

Because in one embodiment the measured values to be transmitted as the first partial set have already been selected before establishing the data transmission, when a communication link exists, the data transmission between the analysis device 2 and the base station 3 can begin immediately. During the data transmission, the analysis device 2 in one embodiment operates as the master and the base station 3 as the slave. For example, the measured value A most recently measured from the first partial set can be transmitted first. It is also possible to transmit another value from the first partial set as the first value, for example, a measured value detected as an outlier. If there is no criterion for transmitting a measured value due to its increased information content, the measured value measured most recently is used.

After the transmission of the first measured value, the base station 3 can optionally output a signal to communicate to the patient that a value has been transmitted. In one embodiment, the patient can himself set whether a communication of the base station 3 is to occur. If a confirmation of this type is desired, it can either be performed after the transmission of the first and/or each further measured value or at the end of the performed data transmission.

If the communication link terminates after the transmission of the first value and/or during the transmission of the further values, the analysis unit 2 operating during the data transmission as the master again becomes the slave and falls back into its rest state after an optional waiting time. The base station 3 again becomes the master, so that the analysis device 2 and the base station 3 always switch back and forth between the function of master and slave.

If the first partial set of the selected measured values was completely transmitted, a confirmation signal can be exchanged between the analysis device 2 and the base station 3. The base station 3 can then request further measured values from the analysis device 2. Alternatively, the analysis device 2 can also transmit further measured values until the entirety of the measured values located in its memory has been transmitted to the base station 3.

For the selection of the first partial set of the measured values, it is to be noted that the total duration of the communication link is always unknown and an early termination must be expected at any time. The selection is therefore, in one embodiment, directed to requirements needed for a medical judgment. For this reason, the values measured directly before the data transmission are frequently of interest. If an outlier value, which lies above a medically established threshold or outside a tolerance band, is determined, this value in one embodiment is transmitted. The tolerance band is predefined in the system and can in one embodiment be changed, for example, by medical personnel. A change by the patient himself is typically not desired, but possible.

The selection of further measured values can be made as a function of an already selected measured value. This dependent selection is useful in particular if the selected value is characterized as outlier. The further measured values are in one embodiment selected using a fixed time raster within an interval around an outlier measured value, which lies outside a predefined tolerance band. All measured values within an interval around the outlier measured value are in one embodiment selected.

Figure 3:
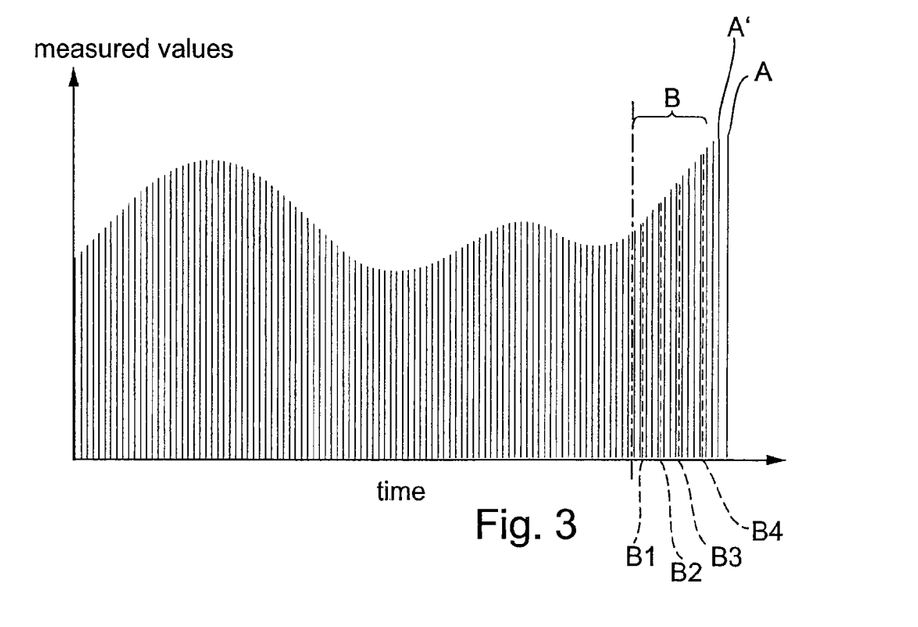
FIG. 3 shows a time curve of the measured values using a first selection criterion.

In FIG. 3, the measured values A and A' are considered as outlier values, because they lie above a medically indicated limit. The interval B is then selected by selecting the measured values B1 through B4, indicated by dashed lines. The equidistant selection of the measured values in the interval B provides an overview of the value curve in this period of time and allows a rise or a drop toward the outlier value A, A' to be recognized. Here as well, the data transmission can begin with the most recent value and be continued as long as the communication link exists.

Figure 4:
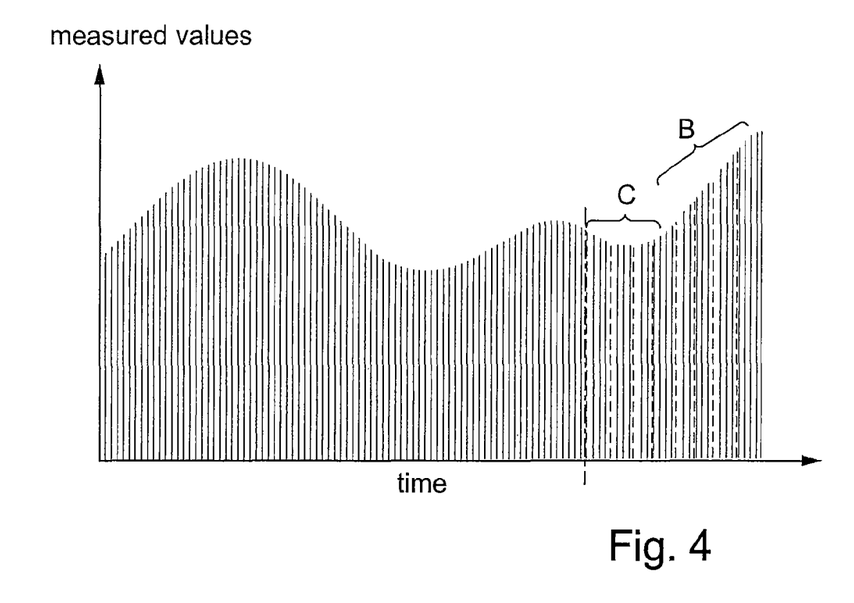
FIG. 4 shows a time curve of the measured values using a second selection criterion.

In order to obtain an expanded overview, following the interval B, a further interval C is established, in which values are also selected using an equidistant raster. The overview is thus expanded over the entirety of the values. A procedure of this type is illustrated in FIG. 4.

The entirety of the measured values stored in the memory is divided into multiple intervals, wherein the first partial set being composed of measured values of these intervals. The measured values are selected with a variable density from the intervals in such a manner that weighting of the intervals is achieved. The selection of measured values using different weighting from various intervals is useful if it is known from the history that outlier measured values can arise more frequently in specific time intervals. A relatively higher density of measured values is then selected from these intervals than from other intervals, which have been shown to be less critical in the past.

For example, the entirety of the stored measured values can be divided into two intervals, the measured values of the first interval being more recent than the measured values of the second interval. The first partial set is selected in such a manner that the density of the measured values selected from the first interval is greater than the density of the measured values selected from the second interval. It is thus taken into consideration that the more recent measured values typically contain a higher information content. In particular if the measured values are used for the purpose of dosing the insulin delivery, the more recent measured values are of greater interest than measured values lying further back.

Figure 5:
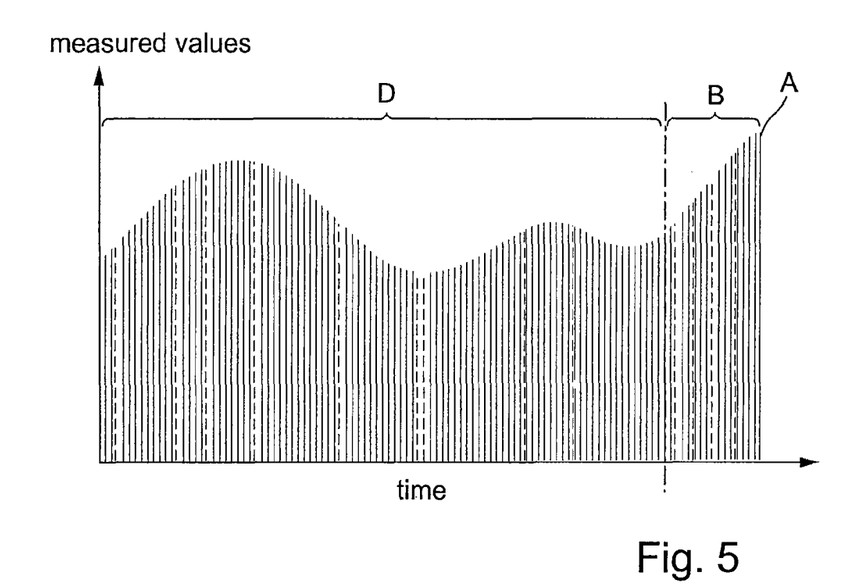
FIG. 5 shows the time curve using a third selection criterion.

The division of the entirety of the stored measured values into two intervals is shown in FIG. 5. The interval B comprises a first number of more recent measured values. The measured values assembled in the interval B reflect approximately 15% of the entirety of the measured values in the example shown. From this 15%, the four measured values B1 through B4 are selected. The interval D comprises the remaining 85% of the measured values. A total of 9 measured values, indicated by dashed lines, are selected from this interval. The absolute number of the measured values selected from the interval D is greater than the number of the measured values from the interval B; nonetheless, the density of the selected values from the interval B is higher.

FIG. 5 shows that in the interval B, the measured values are selected using a constant raster, while in the interval D, the measured values are selected using a raster which is based on a probability function. The time intervals of the selected measured values are not equidistant here.

Figure 6:
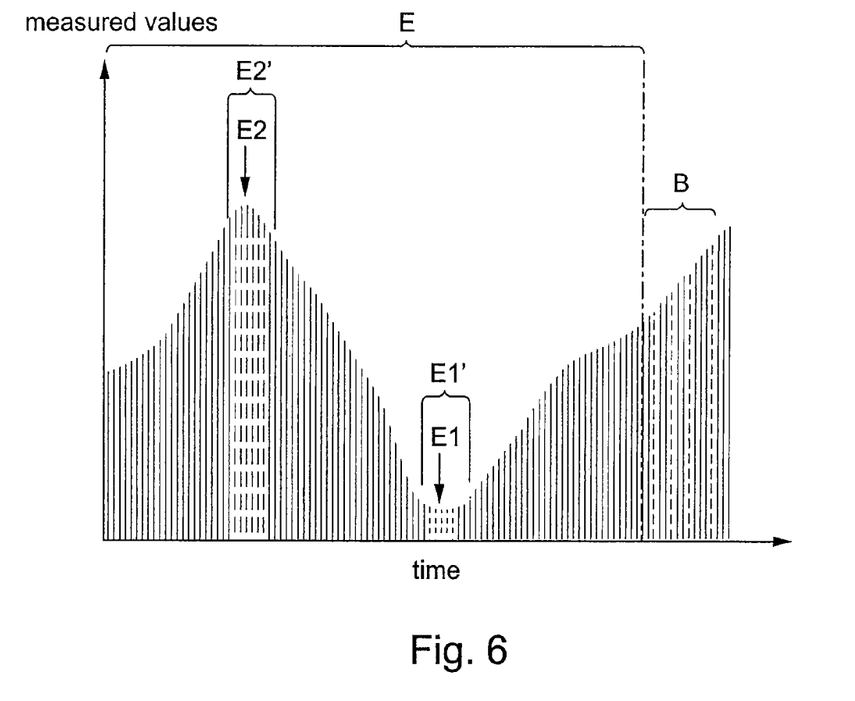
FIG. 6 shows the time curve using a fourth selection criterion.

FIG. 6 shows the case in which, with a division of the entirety of the measured values into two intervals B, E, in the second interval E, two measured values E1 E2 were selected, which were characterized as outliers, because they lie outside a tolerance band. Although the selection of the measured values in interval E is performed using a variable raster, after detecting that the measured values E1 and E2 are outliers, the selection strategy is changed in such a manner that an interval E1' and E2', in which the measured values are selected using a constant raster, is formed around each of the outlier measured values E1, E2. In the present case, all measured values are selected within the intervals E1' and E2'. The analysis system can thus react very flexibly to outlier measured values. The high information content which the outlier values and the neighboring values are based on is considered in the selection of the first partial set. The selected measured values of the first partial set represent the entirety of the measured values precisely sufficiently enough to already make a statement about all measured values from the first partial set of the measured values, for example, to be able to judge the health status of the patient or the system status of an insulin pump.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A diabetes care system for use on a person, comprising:
a base station having a communication unit for wirelessly receiving data, a memory unit for storing transmitted data, and optionally an output unit for displaying the transmitted data; and
a mobile component configured to be carried by the person and including, a continuous measurement unit implantable in the person for measuring relevant data for treatment of diabetes mellitus, a memory for storing the measured data for the treatment of diabetes mellitus, a communication unit for wirelessly transmitting the measured data for treatment of diabetes mellitus to the base station, and a processor programmed to control a selection algorithm, and cooperatively operable with the communication unit to selectively perform a data transmission in such a manner that within a first time interval, in which a wireless communication link between the mobile component and the base station exists, a first partial set, selected from all of the measured data for treatment of diabetes mellitus stored in the memory of the mobile component, is transmitted from the mobile component to the base station, and the first partial set is selected using the processor-controlled selection algorithm,
wherein the selection algorithm selects a subset of the measured data for treatment of diabetes mellitus using a variable time raster without analyzing all of the measured data for treatment of diabetes mellitus stored in the mobile component, identifies one or more outlier values in the subset of data which lie outside a predefined and changeable tolerance band and further selects data from the subset of measured data within a time interval around each of the outlier values using a constant time raster, such that the first partial data set includes the further selected data.

2. The diabetes care system according to claim 1, wherein the processor of the mobile component is programmed such that the first partial set of the data is selected before beginning the data transmission.

3. The diabetes care system according to claim 1, wherein the processor of the mobile component is programmed such that at least a part of the first partial set of the data is transmitted to the base station in a sequence which is reversed from the sequence of its generation.

4. The diabetes care system according to claim 1, wherein an alarm unit is provided as part of the base station to output an optical and/or acoustic warning message if the number of transmitted items of data falls below a lower limit.

5. The diabetes care system according to claim 1, wherein a number of data of the first partial set which have been transmitted by the mobile component to the base station is registered in the mobile component and/or in the base station.

6. The diabetes care system according to claim 1, wherein the processor of the mobile component is programmed such that transmitted data are erased from the memory of the mobile component.

7. The diabetes care system according to claim 1, wherein the mobile component is wearable in order to be carried by the person.

8. A method for selective data transmission within a diabetes care system, comprising:
providing a diabetes care system for use on a person, which comprises
a base station having a communication unit for wirelessly receiving data, a memory unit for storing transmitted data, and optionally an output unit for displaying the transmitted data, and
a mobile component configured to be carried by the person and including a continuous measurement unit implantable in the person for measuring relevant data for treatment of diabetes mellitus, a memory for storing the measured data for treatment of diabetes mellitus, a communication unit for wirelessly transmitting the measured data for treatment of diabetes mellitus to the base station, and a processor being programmed to control a selection algorithm, and cooperatively operates with the a communication unit to
selectively perform a data transmission in such a manner that within a first time interval, in which a wireless communication link between the mobile component and the base station exists, a first partial set, selected from all of the measured data for treatment of diabetes mellitus stored in the memory of the mobile component, is transmitted from the mobile component to the base station, and the first partial set is selected using the processor-controlled selection algorithm;
selecting a first partial set of the measured data for treatment of diabetes mellitus by means of the processor-controlled selection algorithm, using a variable time raster without analyzing all of the measured data for treatment of diabetes mellitus stored in the mobile component,
identifying one or more outlier values in the subset of data which lie outside a predefined and changeable tolerance band and
further selecting data from the subset of data within a time interval around each of the outlier values using a constant time raster, such that the first partial data set includes the further selected data; and
transmitting the first partial set of the data from the mobile component to the base station within the first time interval.

* * * * *

UNITED STATES PATENT AND TRADEMARK OFFICE
CERTIFICATE OF CORRECTION

| | | |
|---|---|---|
| PATENT NO. | : 9,554,703 B2 | Page 1 of 1 |
| APPLICATION NO. | : 11/763004 | |
| DATED | : January 31, 2017 | |
| INVENTOR(S) | : Jurgen Rasch-Menges et al. | |

It is certified that error appears in the above-identified patent and that said Letters Patent is hereby corrected as shown below:

On the Title Page
(30) Foreign Application Priority Data
"06012693" should be --06012693.5--

Signed and Sealed this
Sixth Day of June, 2017

Michelle K. Lee
*Director of the United States Patent and Trademark Office*